United States Patent [19]

Shah et al.

[11] Patent Number: 6,004,996
[45] Date of Patent: Dec. 21, 1999

[54] TETRAHYDROLIPSTATIN CONTAINING COMPOSITIONS

[75] Inventors: Navnit Hargovindas Shah, Clifton, N.J.; Max Zeller, Füllinsdorf, Switzerland

[73] Assignee: Hoffman-La Roche Inc., Nutley, N.J.

[21] Appl. No.: 09/003,137

[22] Filed: Jan. 6, 1998

Related U.S. Application Data

[60] Provisional application No. 60/037,384, Feb. 5, 1997.
[51] Int. Cl.⁶ .......................... A61K 31/335; A61K 9/48; A61K 9/20
[52] U.S. Cl. .......................... 514/449; 424/452; 424/465
[58] Field of Search .......................... 514/449; 424/452, 424/465

[56] References Cited

U.S. PATENT DOCUMENTS

| | | |
|---|---|---|
| 4,598,089 | 7/1986 | Hadvary et al. . |
| 5,540,917 | 7/1996 | Isler et al. . |
| 5,643,874 | 7/1997 | Bremer et al. . |

FOREIGN PATENT DOCUMENTS

| | | |
|---|---|---|
| 638 317 | 2/1995 | European Pat. Off. . |
| 9209271 | 6/1992 | WIPO . |

OTHER PUBLICATIONS

CAPLUS abstract, AN 1995: 422878, Bremer et al. (EP 638 317 A1), (1995).
J.W. Connie and H.R. Hadley, D&CI, Apr. 19970, pp. 38–41.
A. D. Reynolds, Manufacturing Chemist & Aerosol News, Jun. 1970, pp. 40–43.
C.W. Woodruff & N.O. Nuessle, J. Pharm. Sci. 61(5), pp. 787–790 (1972).
H.J. Malinowski & W.E. Smith, J. Pharm. Sci. 64(10), pp. 1688–1692 (1975).
Digestion 52(2) 82–83, 1992, Fried. M.
Diabetologia 36 (Suppl. 1) Abstract A184, 1993, No. 706.
Diabetes Care (USA) 19/11, pp. 1311–1315 (1996).
Diabetes Care (USA) 18/8, pp. 1215–1219 (1995).

*Primary Examiner*—M. Moezie
*Attorney, Agent, or Firm*—George W. Johnston; William H. Epstein; John P. Parise

[57] ABSTRACT

Product containing tetrahydrolipstatin as the active ingredient and pharmaceutically acceptable excipients, characterized in that it is in the form of particles with a diameter of 0.25 to 2 mm; and pharmaceutical preparation s or compositions for oral administration containing the product.

15 Claims, No Drawings

TETRAHYDROLIPSTATIN CONTAINING COMPOSITIONS

This application is a continuation of provisional application No. 60/037,384, filed Feb. 5, 1997.

Background of the Invention

Tetrahydrolipstatin ("THL") is an inhibitor of pancreatic lipase and is known by the generic name orlistat. The use of THL as medicament, particularly as anti-obesity agent, and pharmaceutical compositions containing THL as active agent are described in U.S. Pat. No. 4,598,089.

Due to its low melting point of about 44° C., THL undergoes both hydrolytic and thermal degradation, particularly when stored in a humid atmosphere or above 35° C. in a dry atmosphere. Furthermore, conventional dosage forms such as described in U.S. Pat. No. 4,598,089, for example, tablets or hard gelatin capsules, cannot easily be formulated from powder mix or by conventional wet granulation procedure due to picking and sticking phenomena during tablet compression or encapsulation. Thus, there was a need for THL containing products and dosage forms which would be stable against moisture and heat during production and storage.

SUMMARY OF THE INVENTION

In one of its aspects, the present invention relates to a product containing THL as active ingredient, stabilizers, pharmaceutically acceptable excipients, characterized in that it is in the form of particles with a diameter in the range of from about 0.25 mm to about 2 mm.

These particles are typically in the form of particles or pellets. The preferred pellet form requires the presence of microcrystalline cellulose. Preferably, the diameter of the pellets ranges from about 0.5 to about 1.5 mm.

Surprisingly, it was found that THL containing particles do not feature the sticking and picking phenomena and exhibit superior THL stability.

DETAILED DESCRIPTION OF THE INVENTION

The subject invention will now be described in terms of its preferred embodiments. These embodiments are set forth to aid in understanding the invention but are not to be construed as limiting.

The subject invention provides particles, such as granules and pellets, useful in producing pharmaceutical compositions, such as a unit dosage form. The use of particles in the form of pellets is preferred.

Surprisingly, it was found that THL containing particles (also called multiple units) minimize the sticking and picking phenomena encountered during tablet compression or encapsulation. In one of its aspects, the present invention relates to a unit dosage form comprising a plurality of pellets having a diameter in the range of from 0.25 to 2 mm wherein each particle comprises tetrahydrolipstatin, a stabilizer and at least one pharmaceutically acceptable excipient. When the particles are in the form of pellets, it is critical to employ microcrystalline cellulose.

The term "stabilizer" refers to an agent having a rate of moisture uptake greater than the rate of moisture uptake for THL. Such stabilizer acts to retard hydrolytic degradation of the THL. Preferably, the stabilizer has a moisture content of greater than five percent (5%) at fifty percent (50%) relative humidity. The selection of a stabilizer having the above quantities is within the skill of the artisan having read the present specification. Examples of such stabilizers include, but are not limited to, hydroxypropylmethyl cellulose, hydroxypropyl cellulose, polyvinylpyrrolidone, and lactose.

Preferably, the average diameter of the particles ranges from 0.5 to 1.5 mm. Diameters referred to throughout the specification are average diameters. Although it is preferred that all particles are within the recited ranges, it is acceptable for very minor or trace amounts of undersize or oversize particles to be present.

A further object of the invention is a product as described above which comprises a specific combination of THL with stabilizers, and excipients, particularly a product which contains polyvinylpyrrolidone and/or lactose as stabilizers.

Preferably, the product contains either (a) lactose and at least 3% by weight of the product is polyvinylpyrrolidone or (b) at least 5% by weight of the product is polyvinylpyrrolidone.

Preferred compositions typically contain from about 20% to about 75% by weight THL, and from about 3% to about 60% by weight stabilizer. Preferred pellets additionally contain from about 10% to about 60% by weight microcrystalline cellulose. More preferably, such pellets contain about 25% to about 75% by weight THL; from about 20% to about 60% by weight microcrystalline cellulose; from about 1% to about 10% by weight sodium starch glycolate; from about 1% to about 8% by weight sodium lauryl sulfate; from about 1% to about 10% by weight polyvinylpyrrolidone; and from about 0% to about 1% by weight talc.

Most preferably, such pellets contain about 50% by weight THL; about 39% by weight microcrystalline cellulose; about 3% by weight sodium starch glycolate; about 3% by weight sodium lauryl sulfate; about 5% polyvinyl pyrrolidone; and about 0.1% by weight talc.

Such products are chemically stable and can be filled on fast running encapsulation machines without presenting the sticking and picking phenomena In addition to the preferred stabilizers, polyvinylpyrrolidone and/or lactose, the product of the invention (the particles) contains other excipients, such as diluting agents, for example, sucrose or preferably microcrystalline cellulose (mandatory for pellets of the present invention); binders, for example, starch paste; surfactants, for example, sodium lauryl sulfate or sodium dioctylsulfosuccinate; and/or disintegrants, for example, sodium starch glycolate. The pellets can also contain corn starch as a diluent and disintegrant, and triglycerides.

Pellets are preferably prepared by extrusion of a wet mass followed by spheronization. They can also be prepared by granulation on a rotating base plate in fluidized bed equipment, by agglomeration granulation on an inclined disc equipment, or in high shear mixers.

The process for preparing the pellets is known per se. See, for example, J. W. Conine and H. R. Hadley, D & CI, April 1970, p. 38–41: Small Solid Pharmaceutical Spheres; A. D. Reynold, Manufacturing Chemist & Aerosol News, June 1970, p. 40–43: A new technique for the production of spherical particles; C. W. Woodruff and N. O. Nuessle, J. Pharm. Sci. 61 (5), p. 787–790 (1972): Effect of Processing Variables on Particles obtained by Extrusion-Spheronization Processing; and H. J. Malinowski and W. E. Smith, J. Pharm. Sci. 64 (10), p. 1688–1692 (1975); Use of Factorial Design to Evaluate Granulations Prepared by Spheronization.

Typically, the pelletization process by extrusion and spheronization comprises the following unit operations:

wetting and kneading a powder mass containing the active substance THL and additional excipients with an appropriate, mostly aqueous solution of an appropriate binder to get a wet, pasty mass. Alternatively, the binder may be contained in the powder mix before wetting and kneading;

forcing this wetted mass by means of an appropriate equipment (extruder) through tiny holes of a perforated plate, to get spaghetti-like, wet strands. The diameter of the holes may vary within wide limits, for example, between 0.4 and 1.0 mm, according to the specific product to be obtained.

breaking the strands into short pieces which are at the same time formed to more or less spherical particles by means of a fast spinning, mostly structured plate, in a vertical cylinder (spheronizer).

drying the wet spheres by means of any suitable drying equipment, for example, a fluid bed dryer or a tray drier.

optionally, the dried spheres may be fractionated into appropriate sized fractions, or the main material may be freed from undersized or oversized material by an appropriate sieving or screening process. Preferably, the temperature is maintained below 35° C. during the whole process.

A further aspect of the invention are pharmaceutical preparations or compositions for oral administration, comprising the particles. They can be simply filled in a PVC container from which the particles can be taken with a dosing spoon. Other oral dosage forms are sachets in which the particles are filled, alone or together with appropriate excipients, such as skim milk powder, microcrystalline cellulose, sodium carboxymethylcellulose and talc, to form a powder for reconstitution. Another possibility is to embed the particle in a matrix excipient, for example, microcrystalline cellulose, followed by compression to tablets, particularly chewable tablets. The particle, can also be filled in capsules, for example, hard gelatin capsules.

The following Examples are illustrative but in no way limit the invention.

EXAMPLE 1

Preparation of Pellets

The following applies to a batch size of 4.0 kg pellets.

a) 120 g sodium lauryl sulfate and 200 g polyvinylpyrrolidone (Povidone) are dissolved under stirring in q.s. demineralized water. The solution is cooled to 10–15° C. (solution A).

b) 2000 g THL, 1560 g microcrystalline cellulose and 120 g sodium starch glycolate are charged to a high speed mixer DIOSNA, type P50) and pre-mixed for 1 minute with mixer and chopper at the low speed position "I" (pre-mix B).

c) Solution A is charged to the pre-mix B and kneaded for 2.5 minutes at mixer and chopper position "I", then the chopper is set to position "II". After 3 minutes the chopper position is again reduced to "I" for 1 minute, then the material is discharged through the outlet valve; its temperature is then between 20 and 25° C. (C).

d) The material is fed to an extruder (NICA Lab, type E-140). The extruder is equipped with a screen with 0.8 mm nominal mesh size and thickness 1.0 mm; the screen is surrounded by a cooling device. The material is extruded to spaghettis of appropriate length. The temperatures of the extrudate and of the extruder screen are below 35° C. (extrudate D).

e) The extrudate D is transferred in sub-batches of approx. 800 g to a spheronizer (NICA Lab type S-320) and spheronized for ¾–2 minutes at 700 rpm (wet pellets E).

f) The cylinder-shaped, wet pellets E are transferred to a fluidized bed dryer (AEROMATIC, type MP-1), equipped with a dry air supply, and dried at an incoming air temperature below 35° C. to a low final moisture content of the pellets (F).

g) The dried pellets are sieved by means of a square sieve with sieve inserts 0.50 mm and 1.25 mm mesh size; the undersize-and oversize fractions are discarded; the fractions 0.5–1.25 mm are collected as THL pellets in tightly closed containers. See pellets A in Table 1 below.

EXAMPLE 2

Preparation of Pellets

The following applies to a batch size of 6.0 kg pellets.

a) 180 g sodium lauryl sulfate and 300 g Povidone are dissolved in q.s. demineralized water by means of a stirrer. The solution is cooled down to approx. 10–15° C. by putting the beaker into a mixture of ice and water (A).

b) 1800 g THL, 3120 g microcrystalline cellulose and 600 g sodium starch glycolate are given to a high speed mixer (DIOSNA, type P50) and pre-mixed for 1 minute with mixer and chopper at the low speed position "I" (B).

c) Solution A is given to the pre-mix B and kneaded for 2.5 minutes at mixer and chopper position "I", then the chopper is set to position "II". After 3 minutes, the chopper position is again reduced to "I" for 1 minute, then the material is discharged through the outlet valve; its temperature is then between 20 and 25° C. (C).

d) The material is fed to an extruder and treated as in Example d).

e) The resulting extrudate is transferred in sub-batches of approx. 800 g to a fluidized bed dryer (AEROMATIC, type MP-1), equipped with a roto-granulation device and a dry air supply, and spheronized for 3 minutes at 500 rpm (E).

f) The cylinder-shaped, wet pellets E are then dried in the same equipment, at an incoming air temperature below 35° C., to a low final moisture content of the pellets (F).

g) The dried pellets F are sieved by means of a square sieve with sieve inserts of 0.50 mm and 1.25 mm mesh size; the undersize- and oversize-fractions are discarded; the fractions 0.5–1.25 mm are collected as THL pellets in tightly closed containers. See pellets B below.

The compositions of pellets A and pellets B are given in Table 1:

TABLE 1

| Pellet Formulation (in weight-%) | A | B |
|---|---|---|
| Active Drug: | | |
| THL finely milled | 50.0 | 30.0 |
| Excipients: | | |
| Microcrystalline cellulose | 39.0 | 52.0 |
| Sodium starch glycolate | 3.0 | 10.0 |
| Sodium lauryl sulfate | 3.0 | 3.0 |
| Povidone | 5.0 | 5.0 |
| Total | 100.0 | 100.0 |

EXAMPLE 3

Preparation of Pellets

Pellets with the following compositions were prepared in a manner similar to that of pellets A and B:

TABLE 2

| Pellet Formulation (in weight-%) | F1 | F2 | F3 | F4 | F5 | F6 |
|---|---|---|---|---|---|---|
| THL | 29.1 | 30.2 | 50 | 50 | 50 | 50 |
| Lactose | 33.5 | 34.0 | 7 | 21 | 12 | |
| Microcrystalline cellulose | 23.6 | 20.8 | 36 | 19.5 | 21 | 41 |
| Sodium starch glycolate | 9.1 | 9.4 | 3 | 3 | 9.5 | 3 |
| Sodium lauryl sulfate | 1.1 | 1.1 | 1 | 1 | 3 | 1 |
| (Povidone) Polyvinylpyrrolidone | 3.6 | 4.5 | 3 | 3 | 4.5 | 5 |
| Medium chain triglyceride | | | | 2.5 | | |

EXAMPLE 4

Preparation of Final Dosage Form

The pellets A or B (of Examples 1 and 2 above) are either mixed with talc and encapsulated on equipment provided with a pellet fill station (formulations C, E);

or a mixture of pellets A or B with skim milk powder, microcrystalline cellulose and talc is filled into sachets (formulation D).

A similar mixture is compressed to chewable tablets (formulation F).

The compositions of the final dosage forms C, D, E, F are given in Table 3.

TABLE 3

Final Dosage Form Compositions (in mg per dose)

| Formulation | C | D | E | F | |
|---|---|---|---|---|---|
| Final Active Drug Content | 120.0 | 60.0 | 30.0 | 30.0 | mg |
| Active Drug in Form of Pellets: | | | | | |
| Pellets A | 240.0 | 120.0 | — | — | mg |
| Pellets B | — | — | 100.0 | 100.0 | mg |
| Excipients: | | | | | |
| Skim milk powder (granulated) | | 3875.0 | | | mg |
| Microcrystalline cellulose + sodium carboxymethyl-cellulose (AVICEL RC-types) | | 1000.0 | | | mg |
| Microcrystalline cellulose | | | | 1888.0 | mg |
| Talc | 0.24 | 5.0 | 0.1 | 2.0 | mg |
| Magnesium stearate | | | | 10.0 | mg |
| Total Hard Gelatin Capsule Fill weight | 240.24 | | 100.1 | | mg |
| Total Sachet Fill Weight | | 5000.0 | | | mg |
| Chewable Tablet Weight | | | | 2000.0 | mg |

The detailed composition of formulation C for capsules filled with pellets A is as in Table 4:

TABLE 4

Production Batch Size = 160.160 kg = 666,666 capsules
Fill Weight = 240.24 mg

| Ingredient | Quantity mg/Capsule | 666,666 Capsules Contain (kg) |
|---|---|---|
| THL | 120.00 | 80.000 |
| Microcrystalline cellulose (AVICEL PH-101) | 93.60 | 62.400 |
| Sodium starch glycolate (PRIMOJEL) | 7.20 | 4.800 |
| Sodium lauryl sulfate | 7.20 | 4.800 |
| Polyvinylpyrrolidone (Povidone) (K-30) | 12.00 | 8.000 |

TABLE 4-continued

Production Batch Size = 160.160 kg = 666,666 capsules
Fill Weight = 240.24 mg

| Ingredient | Quantity mg/Capsule | 666,666 Capsules Contain (kg) |
|---|---|---|
| Talc | 0.24 | 0.160 |
| Total | 240.24 mg | 160.160 kg |

EXAMPLE 5

Preparation of Granules and Formulations Containing THL

| Ingredient | mg/capsule |
|---|---|
| 1. THL | 120 |
| 2. Microcrystalline cellulose | 93.6 |
| 3. Sodium starch glycolate | 7.2 |
| 4. Polyvinyl pyrrolidone | 12.0 |
| 5. Sodium lauryl sulfate | 7.2 |
| Total | 240.00 |

1. Polyvinyl pyrrolidone and sodium lauryl sulfate is dissolved in water.
2. THL, microcrystalline cellulose, and sodium starch glycolate are mixed for 10 minutes and granulated with the solution of step 1.
3. Granules are dried at or below 30° C. and passed through # 20 mesh screen.
4. Granules are filled in a # 1 hard gelatin capsule.

EXAMPLE 6

Preparation of Granules and Formulations Containing THL

| Ingredient | mg/capsule |
|---|---|
| 1. THL | 120 |
| 2. Lactose anhydrous | 93.6 |
| 3. Sodium starch glycolate | 7.2 |
| 4. Polyvinyl pyrrolidone | 12.0 |
| 5. Sodium lauryl sulfate | 7.2 |
| Total | 240.00 |

1. Polyvinyl pyrrolidone and sodium lauryl sulfate is dissolved in water.
2. THL, lactose anhydrous, and sodium starch glycolate is mixed for 10 minutes and granulated with the solution of step 1.
3. Granules are dried at or below 30° C. and passed through #20 mesh screen.
4. Granules are filled in a # 1 hard gelatin capsule.

The subject invention has been described in terms of its preferred embodiments. Upon reading the specification, a skilled artisan will become cognizant of various alternative embodiments. These variations are to be considered within the scope and spirit of the invention which is only to be limited by the claims that follow and their equivalents.

What is claimed is:

1. A pharmaceutical composition comprising a plurality of pellets having a diameter in the range of from about 0.25 mm to about 2 mm, and at most only a trace amount of pellets outside this range, each pellet comprising about 50% by weight tetrahydrolipstatin; polyvinylpyrrolidone; microcrystalline cellulose; and at least one pharmaceutically acceptable excipient.

2. The composition of claim 1, wherein the pellets have a diameter of from about 0.5 mm to about 1.5 mm.

3. The composition of claim 1, wherein at least 5% by weight of the composition is polyvinylpyrrolidone.

4. The composition of claim 1, wherein the pharmaceutically acceptable excipient is a surfactant, diluent, or disintegrant.

5. The composition of claim 4, wherein the pharmaceutically acceptable excipient is a surfactant.

6. The composition of claim 5, wherein the surfactant is sodium lauryl sulfate or sodium dioctylsulfosuccinate.

7. The composition of claim 4, wherein the pharmaceutically acceptable excipient is a diluent.

8. The composition of claim 7, wherein the diluent is sucrose or corn starch.

9. The composition of claim 4, wherein the excipient is a disintegrant.

10. The composition of claim 9, wherein the disintegrant is sodium starch glycolate, cross-linked polyvinyl pyrrolidone, cross-carmolose sodium, or a hydroxypropyl cellulose.

11. The composition of claim 1 which comprises about 50% by weight tetrahydrolipstatin; about 39% by weight microcrystalline cellulose; about 3% by weight sodium starch glycolate; about 3% by weight sodium lauryl sulfate; about 5% by weight polyvinylpyrrolidone; and about 0.1% by weight talc.

12. The composition of claim 1 which is in unit dosage form.

13. The composition of claim 11 which is in unit dosage form.

14. The composition of claim 1 which comprises about 120 mg of tetrahydrolipstatin; about 93.6 mg of microcrystalline cellulose; about 7.2 mg of sodium starch glycolate; about 7.2 mg of sodium lauryl sulfate; about 12 mg of polyvinylpyrrolidone; and about 0.24 mg of talc.

15. The composition of claim 14 which is in unit dosage form.

* * * * *